United States Patent [19]

Talish et al.

[11] Patent Number: 4,550,714
[45] Date of Patent: Nov. 5, 1985

[54] ELECTROMAGNETIC COIL INSERT FOR AN ORTHOPEDIC CAST OR THE LIKE

[75] Inventors: Roger J. Talish, Fairfield; Victor F. Banko, Dover, both of N.J.

[73] Assignee: Electro-Biology, Inc., Fairfield, N.J.

[21] Appl. No.: 473,801

[22] Filed: Mar. 9, 1983

[51] Int. Cl.[4] ............................................. A61N 1/40
[52] U.S. Cl. .................................... 128/1.5; 128/82.1; 128/419 F; 128/802
[58] Field of Search ................. 128/1.3, 1.5, 82.1, 128/419 F, 303.13, 303.14, 783, 798, 802, 804, 641; 219/10.79; 336/66

[56] References Cited

U.S. PATENT DOCUMENTS

| | | | |
|---|---|---|---|
| 4,166,465 | 9/1979 | Esty et al. | 128/303.13 |
| 4,197,851 | 4/1980 | Fellus | 128/798 X |
| 4,200,104 | 4/1980 | Harris | 128/303.14 |
| 4,257,424 | 3/1981 | Cartmell | 128/641 |
| 4,266,532 | 5/1981 | Ryaby et al. | 128/419 F |
| 4,445,518 | 5/1984 | Eggli et al. | 128/783 |

FOREIGN PATENT DOCUMENTS

| | | | |
|---|---|---|---|
| WO80/01045 | 5/1980 | World Intel. Prop. Org. | 128/804 |
| 618179 | 2/1949 | United Kingdom | 128/804 |
| 2027594 | 2/1980 | United Kingdom | 128/798 |

Primary Examiner—Lee S. Cohen
Attorney, Agent, or Firm—Hopgood, Calimafde, Kalil, Blaustein & Judlowe

[57] ABSTRACT

The invention contemplates integration of electrical componentry into an orthopedic cast, using one or more multiple-twin coils which are essentially flat and thin and flexibly conformable to local curvature of the limb or other body feature to be subjected to electromagnetic therapy. The coil or coils structure is devised for self-retention to the afflicted part of the body, for at least such time as is needed by the orthopedic surgeon to apply a supporting cast to the afflicted region, the coil or coils being a rigid ultimately expendible part of the cast. Provision is made for rigid cast support of an externally accessible electrical connector for excitation of the coil or coils with electrical signals having therapeutically beneficial coupling to the afflicted region, via induction from magnetic-field radiation by the coil or coils.

19 Claims, 11 Drawing Figures

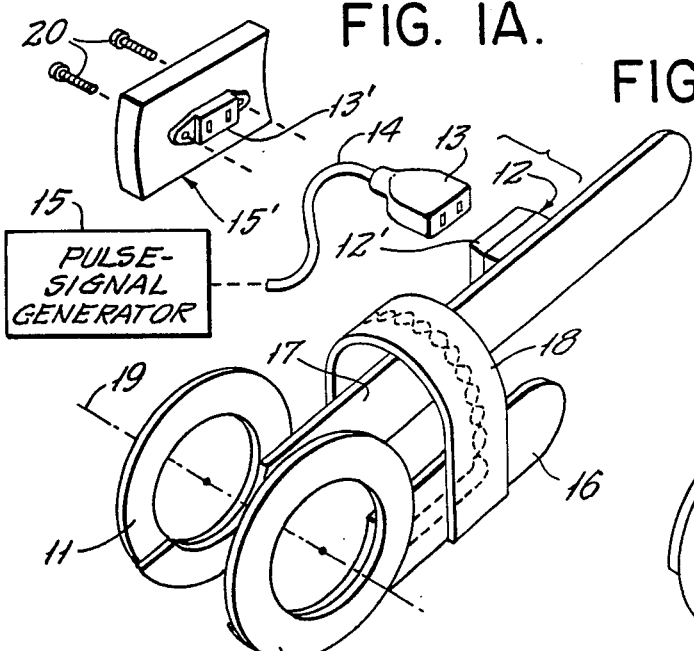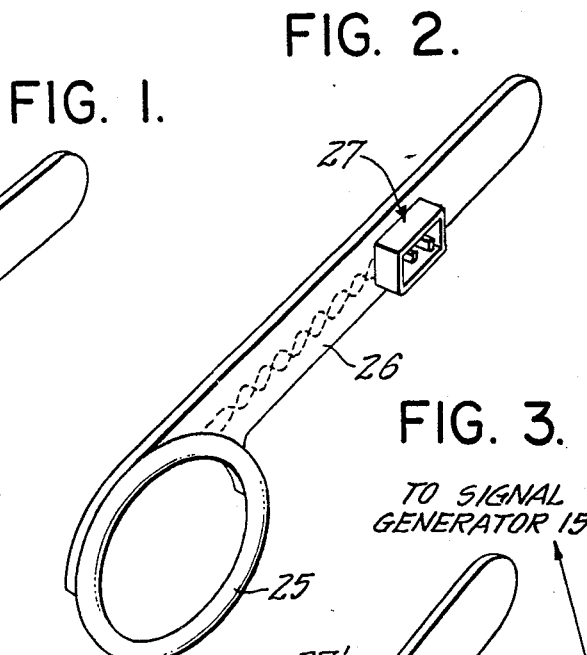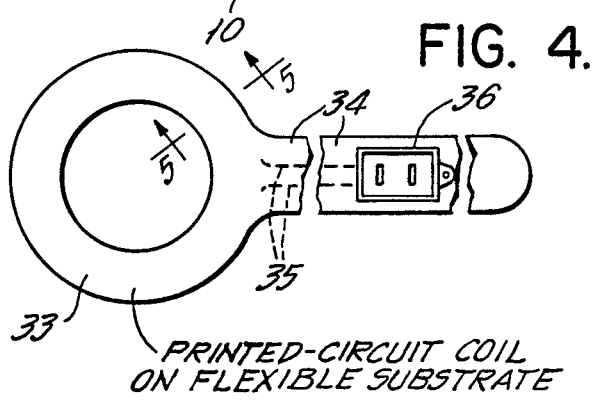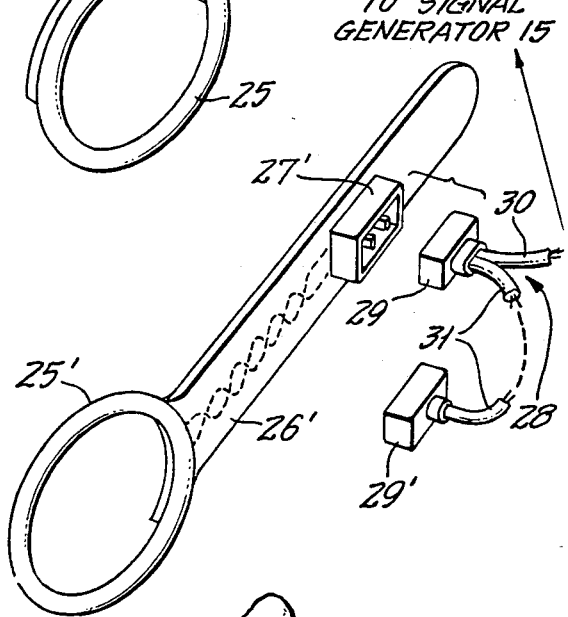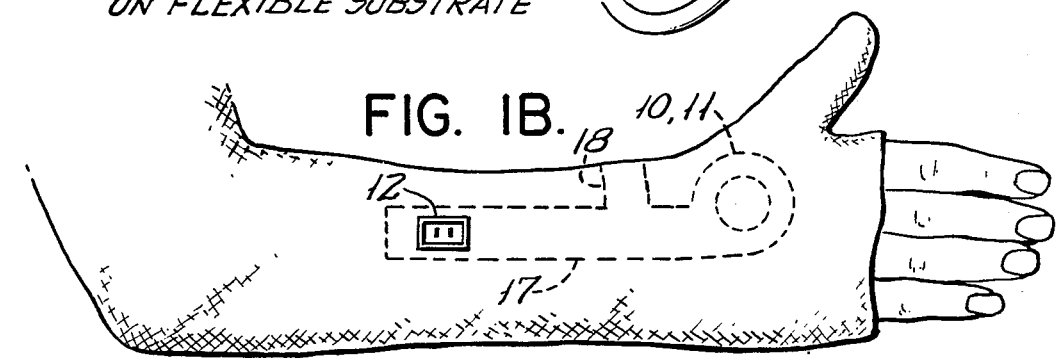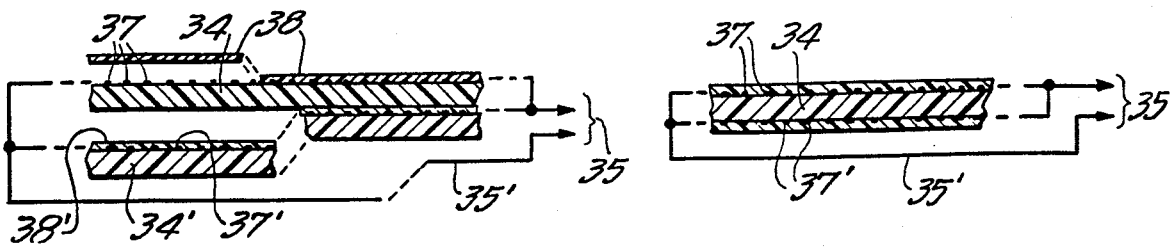

ELECTROMAGNETIC COIL INSERT FOR AN ORTHOPEDIC CAST OR THE LIKE

BACKGROUND OF THE INVENTION

This invention relates to the treatment of living tissues and/or cells by altering their interaction with charged species in their environment. More particularly, the invention relates to an electromagnetic body-treatment device for surgically noninvasive modification of the growth, repair and maintenance behavior of living tissues and cells by a specific and selective change in electrical environment.

Ryaby, et al., U.S. Pat. Nos. 4,105,017, 4,266,532 and 4,266,533 describe means for effecting surgically non-invasive direct inductive coupling to an afflicted body region, whereby one or more electric voltage and concomitant current signals conform to a highly specific pattern and have been found to develop therapeutically beneficial treatment of the afflicted region, as for example in the enhancement of repair of bone fractures, nonunions, and the like. In general, the involved treatment head or heads have involved one mo more large coils, which have served well for the treatment of large-member bones, as in leg regions. And various special-purpose coil and head configurations have been disclosed for specific treatments. In general, it may be said that it has been preferred practice to employ a treatment-head configuration in which two like coils are electrically connected in flux-aiding relation and have flexibly articulated connection to enable strapped application on opposite sides of an afflicted limb, and with the coils on a common axis of magnetic-flux development through the afflicted region. However, for certain injuries, such as bone injury in the carpalnavicular region of the arm, it becomes very awkward, bothersome, and inconvenient to use the conventional articulated-coil technique, in that use of the arm must be severely curtailed, due primarily to treatment-head considerations.

BRIEF STATEMENT OF THE INVENTION

It is an object of the invention to provide a new approach to treatment-head design in equipment of the character indicated, with a view to reducing bulk and simplifying application to an afflicted region of the body.

It is a specific object to provide as an article of manufacture, an improved treatment-head component, particularly suited to integration with an orthopedic cast.

Another specific object is to provide, as an article of manufacture, coil structure which is directly applicable to an afflicted body part and which is sufficiently pliant to be locally adaptable to the curvature of the body part at the point of application.

A further specific object is to meet the above objects with structure that is self-retaining to the afflicted body part at least for the time needed to complete orthopedic casting in support of the afflicted body part and with the coil structure rigidly integrated into the casting.

A general object is to meet the above objects with structure of elemental simplicity, inherently low cost, and featuring minimum modification of conventional orthopedic casting technique.

The invention achieves the foregoing objects with one or more multiple-turn coils which initially are essentially flat and thin and flexibly conformable to local curvature of the limb or other body feature to be subjected to electromagnetic therapy. The coil or coils structure is devised for self-retention to the afflicted part of the body, in the course of the orthopedic surgeon's application of a supporting cast to the afflicted region, the coil or coils being a rigid ultimately expendible part of the cast. Provision is made for rigid cast support of an externally accessible electrical connector for excitation of the coil or coils with electrical signals having therapeutically beneficial coupling to the afflicted region, via induction from magnetic-field radiation by the coil or coils.

DETAILED DESCRIPTION

The invention will be illustratively described for several embodiments, in conjunction with the accompanying drawings, in which:

FIG. 1 is a view in perspective for a first embodiment of the invention;

FIG. 1A is a view in similar perspective to illustrate alternative signal-supply connection to apparatus of FIG. 1;

FIG. 1B is a view in elevation of an arm cast to which the embodiment of FIG. 1 has been applied;

FIGS. 2 and 3 are similar views to illustrate modifications;

FIG. 4 is a plan view of another embodiment;

FIGS. 5 and 6 are similar enlarged and exaggerated fragmentary sectional views taken at 5—5 in FIG. 4 to illustrate alternative details of construction in FIG. 4;

Figure 7:
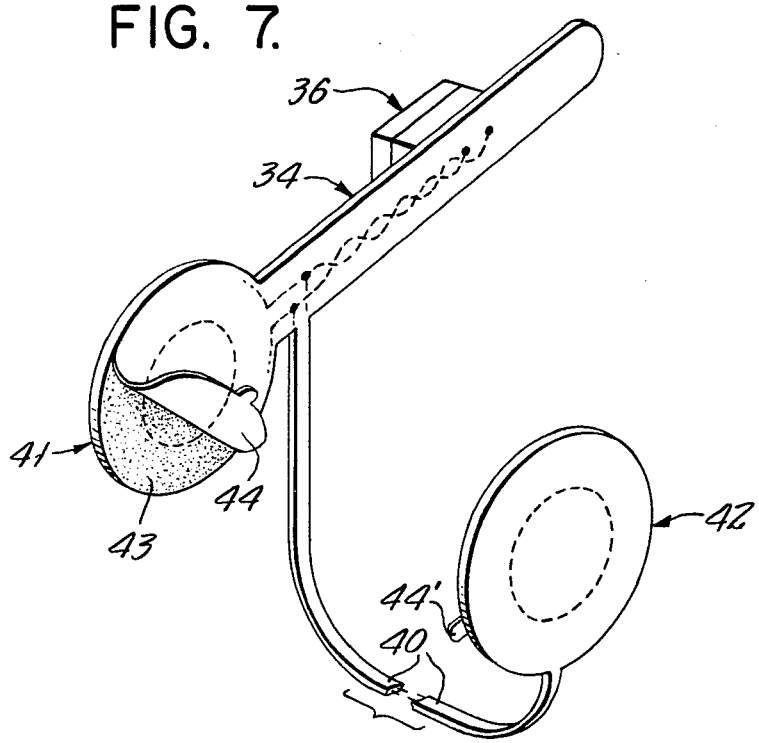
FIG. 7 is a view in perspective to illustrate an assembly representing an alternative for the embodiment of FIG. 1.

In FIG. 1, the invention is shown in application to unit-handling structure which is configurated for self-retention on an afflicted body limb, such as the forearm, and which positions two like electrical coils 10-11 on opposite sides of the specifically afflicted region, as for example, the carpal-navicular region, which will be illustratively assumed to have suffered bone fracture. Each of the coils 10-11 comprises multiple turns of insulated wire, the leads of which will be understood to be interconnected for flux-aiding development of a varying magnetic field of interest, in the space between the coils. These leads will also be understood to be electrically supplied by or via connector means, shown in FIG. 1 as a plug-component unit 12 and plug-receptacle unit 13, detachably connectable to unit 12. The plugreceptacle unit 13 is the output end of a flexible-cable connection 14 to a pulse-signal generator 15. Such a signal generator and the character of signals produced thereby have been described in said Ryaby, et al patents, so that further description thereof is not now needed.

For treatment of bone injury in the carpalnavicular region, the coils 10-11 will be positioned on opposite sides of and directly applied at the wrist, namely over the usual stockinette, cotton padding and initial layer of cast, thus involving a natural spacing of approximately two inches, depending upon the size of the patient's wrist. Each coil suitably comprises 80 turns of enameled 24-AWG wire, initially wound to a thin flat circular annulus, having a 1.5-inch inner diameter and a 2.5-inch outer diameter; the preferred average turns diameter (2 inches) substantially equals or exceeds the maximum spacing between coils, consistent with principles discussed in said Ryaby, et al. patents. Each coil is about ⅛-inch thick, and its general initially formed shape is adequately retained by an overall vinyl coat, the retention (in conjunction with stretchability of the vinyl coat) being such as to enable limited arcuate deformation of the annulus, from the initially formed flat and into local substantial conformation to the patient's adjacent wrist profile.

To unite the described operative components into a single unit-handling structure, each of the coils is bonded to a mounting strip of relatively stiff material which is magnetically transparent and preferably electrically insulating, for example, as cut from vinyl sheeting of about 1/16-inch thickness. Such a strip 16 is bonded to coil 10, and a similar strip 17 is bonded to coil 11; and a more stiffly compliant arched strip 18, as of 1/16-inch thick semi-rigid or suitably stiff plastic, provides connection of strips 16-17, with a measure of bendability, to adapt coil spacing to individual-patient requirements. The width of strips 16-17-18 is suitably ¾ to one inch, and the stiffer connecting strip 18 has bonded overlap with strips 16 and 17 at equal offset from the respective coils, and also at offset from projecting free ends of strips 16 and 17. Connector unit 12 is permanently secured to strip 17, preferably at further offset from strip 18 and also at offset from the free end of strip 17. Described electrical lead connections of coils 10-11 to each other and to connector unit 12 are schematically shown and will be understood to be bonded to outwardly facing surfaces or edges of strips 16-17-18, and the indicated vinyl coat is applied, as by dipping the entire described structure (including coils 10-11) in a fluidized bed. To protect otherwise exposed electricalcontact elements of connector unit 12 during and after the vinyl-coating process, a removable protective cover 12' is shown covering the outwardly facing side of connector unit 12; this cover is removed by the surgeon just prior to applying the coils and their supporting structure to the afflicted arm of the patient.

In use, once the surgeon has selected a FIG. 1 structure of proportions and dimensions appropriate to his patient's requirements, he checks the structure of FIG. 1, to assure that the arch 18 may derive extensively stabilized wrapping contact with an undamaged region of the forearm, to thereby position the axes of coils 10-11 in substantial alignment (19) through the afflicted region to be treated. The surgeon's initial steps will also be understood to involve adjusted wrapping of coils 10-11 for general local conformance to the patient's wrist contour, and the arched stiffness at 18 will be understood to enable temporary retention of adjusted coil and connector assembly to the patient's forearm. Conventional casting now proceeds, to wrap the afflicted forearm at least to the extent of fully embedding coils 10-11 and strips 16-17-18 therein. The only departure from the conventional procedure is to develop the cast around (and not over) connector unit 12 and its cover, and the outer wall height of connector 12 beyond the outer surface of strip 17 is suitably one-half inch, thereby accommodating a conventional cast thickness of similar extent. When the cast has sufficiently cured, cover 12' is removed and plug connection (13) is made to unit 12, whereby generator 15 may be activated to supply coil-excitation, as of the nature described in the Ryaby, et al. patents.

The signal generator 15 may be somewhat bulky and therefore suitably desk or table mounted, with sufficient length of flexible cable 13 to serve the patient with a measure of freedom to move in the course of periodically administered treatment, as may be prescribed. Once connection 12-13 is severed, the patient is free to move with no greater encumbrance than involved with the conventional cast alone. Alternatively, the signal generator may be a miniaturized package, incorporating its own rechargeable battery, and adapted for longer-duration attachment at connector unit 12; such a compact signal generator 15' is shown in FIG. 1A, complete with fixed-receptacle provision at 13', having plug-in compatability with unit 12. The plug-in capability may be via a bayonet-type twist-lock arrangement wherein electrical start-up commenced upon twist into the engaged position, but in the form shown, anchoring bolts 20 pass through spaced bores in bosses of receptacle 13' for threaded reception in spaced tapped holes (not shown) of unit 12, so that the plug-in connection of unit 15' can be positively retained in operative assembly to the cast components; excitation may be inherent in establishing the plug-in connection, or a separate switch (not shown) may be actuated for the purpose. And it will be understood that with suitably headed formation of bolts 20, it is a simple matter for the patient to connect and disconnect the generator 15', as his convenience may dictate, in periods between treatments.

In the embodiment of FIG. 2, a single coil 25 is mounted to one end of an elongate flexible strip 26 to which a connector unit 27 is also mounted. Coil 25 may be initially flat and bendable into body conformation, but as shown, the multiple turns of coil 25 are tightly bundled, rendering coil 25 more rigid than coils 10-11 of FIG. 1. The device of FIG. 2 is therefore more adaptable to treatment of more-flat areas of the body of the patient, but offset relation of connector 27 from coil 25 and from the free end of strip 26 enables a substantial stabilizing embedment of the device either in a cast or in a tight wrap of surgical tape, to anchor the entire device to the body, for treatment within the field of magnetic radiation of coil 25. The tangential application of strip 26 to coil 25 will be understood to afford a measure of alignment offset, as between the elongation axis of strip 26 and the center of coil 25; for other situations, an opposite-sense tangential connection (not shown) or an on-axis alignment (as in FIG. 3) may be more appropriate and, therefore, an inventory of all three of such configurations is recommended.

Coil and connector assemblies as described in connection with FIGS. 2 and 3 may be used singly (applied to a body surface sufficiently proximate to a region to be treated) or in tandem. In the latter event, two single units, as of the FIG. 3 variety, may be positioned along diametrically opposite longitudinal alignments on the same limb, for example the forearm, relying upon adhesive tape for temporary retention of strip 26' to the desired adjacent region of the forearm, such that the axis of coil 25' of one unit generally aligns with the axis of coil 25' of the opposite unit, and such that the aligned axes traverse the afflicted region. The temporary positioning becomes permanent when an enveloping cast is applied and cured to integrate both coils 25' and their strips 26' into a rigid body. And the connector means to signal generator 15 may involve a single flexible-cord set 28 wherein one receptacle element 29 is detachably connected to plug unit 27' and a second receptacle element 29' is detachably connectable to the plug unit (27')

of the second coil in the cast; as shown, a flexible supply cable (30) connection extends between signal generator 15 and receptacle element 29, and a flexible branch cable (31) connection extends between receptacle elements 29-29'.

FIG. 4 illustrates another embodiment in which the spirally developed initially flat coil at annulus 33 is a printed-circuit coil, i.e., as formed on a substrate 34 by photographic, plating, etching, and/or other techniques well established in the printed-circuit art. The planiform of the substrate 34 may correspond to the overall planiform of strip 17 and coil 11 in FIG. 1, thus providing the base (a) for multiturn spiral development of the coil within annulus 33 and (b) for the integrally connected development of spaced leads 35 from the coil and to the region of an externally accessible connector-plug unit 36. The substrate 34 is of electrically insulating, magnetically transparent material and is selected for a degree of body-conforming flexibility which will not impair electrical conductivity of the printed-circuit application thereto. FIGS. 5 and 6 illustrate alternative embodiments of such printed-circuit usage in the structure of FIG. 4.

In FIG. 5, the sectional view cuts a plurality of adjacent turns of the spirally developed coil, and these turns appear as short heavy dashes (37) on one surface of substrate 34. A protective layer 38, such as an adhered film of polyethylene, covers the printed-circuit application. A second printed-circuit coil of spirally developed turns (37') on a circular substrate 34' matches the size and turns of the coil on substrate 34 and is similarly covered with a protective layer 38'. Layer 38' is not only adhered to the printed-circuit side of substrate 34', but it is also adhered to the unprinted side of substrate 34, with the respective printed-coil formations in axial registry. Further plies of printed-circuit coil components may be added to complete the multiple-layer development of a single coil, the electrical rendering into a single coil being by series or parallel connection of the respective radially inner and outer ends of the different layers. In FIG. 5, the two registering printed-circuit coil components on substrates 34-34' are shown connected in parallel and in flux-aiding relation with lead connections 35 adapted for connector unit 36, and the lead 35' to the radially inner connection of the two coil components will be understood to be preferably adhered to the unprinted side of substrate 34', and thus offset away from the layer 38 which will be adjacent the body region to be treated. To aid flexibility of the multiple-layer configuration of FIG. 5, the protective layer 38' via which the two printed substrates are adhered is advisably relatively soft and yieldable and may be a thin application of foamed vinyl. Again, the completed assembly according to FIGS. 4 and 5 may have a final protective coat of vinyl, as described in connection with other embodiments.

In the embodiment of FIG. 6, the single substrate 34 is clad with a printed-circuit coil formation on each of its surfaces, namely, turns 37 of a first coil component and turns 37' of a second coil component, the two components being in axial registry and coextensive with the annulus 33. Protective layers 38-38' cover the respective coil formations, and electrically parallel fluxaiding connections are made to leads 35, as described for FIG. 5.

It will be understood that the multiple-layer development of printed-circuit coil components in FIGS. 5 and 6 is to the extent needed to provide a desired total number of turns for flux development, as deemed necessary for particular size and excitation levels. For example, the above-noted 80-turn illustration in connection with FIG. 1 may be achieved in a printed-circuit configuration according to FIG. 6, wherein twenty-turn expanding spiral coil components are printed on the respective sides of substrate 34, and wherein a duplicate such printed substrate is laminated thereto in axial register, with parallel interconnection of all four of the 20-turn components.

FIG. 7 illustrates a unit-handling alternative to the embodiment of FIG. 1, wherein a flat flexible length of branch cable 40 interconnects two coil units 41-42, which may each be of the flexible printed-circuit variety described in connection with FIGS. 5 and/or 6, except that the strip connection to plug unit 36 is only needed for one (41) and not for the other (42) of the two coil units. In the embodiment of FIG. 7, surfaces adapted for body/stockinette or the like application are coated, as at 43, with a layer of pressure-sensitive adhesive, and a peel-off sheet 44 of release material protects the adhesive until it is needed. The protective sheet 44 over adhesive 43 at coil unit 41 is shown at commencement of peel-off and will be understood to be continuous along the strip connection to and beyond the locale of plug unit 36. Thus, as a first step of using the embodiment of FIG. 7, and after the usual wrap of stockinette and padding is applied, sheet 44 is separated from unit 41, which is then selfadhered to the wrap at the afflicted body region as appropriate for coil-axis positioning. A separate peel-off sheet 44' covers the adhesively coated side of the other coil unit 42 and is removed after the surgeon is satisfied with his location of coil unit 41; care should be taken in manufacture that the adhesively coated side of coil unit 42 is such in relation to the adhesively coated side of unit 41 that with both adhesive coatings facing opposite sides of the afflicted region for treatment, the coils of the respective units 41-42 are connected in flux-aiding relation. Once units 41-42 are self-adhered in desired positions, an orthopedic cast is completed, with embedment of the components 41-42.

Figure 8:
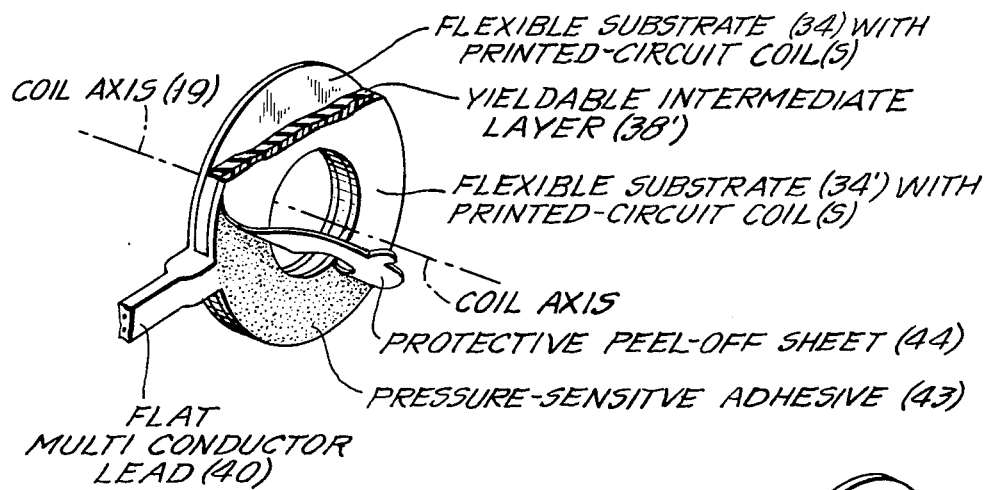
FIG. 8 is a perspective view of a coil-component construction, partly broken-away and shown with exaggeration of thicknesses, for better illustration and labelling of parts.

FIG. 8 is an enlarged exaggerated, and simplified diagram with descriptive legends, to identify components which have already been described, for the case of two laminated substrates 34-34' with a yieldable intermediate layer 38' therebetween. The coil components of layers 34-34' may be as described for FIG. 5 or FIG. 6.

Figure 9:
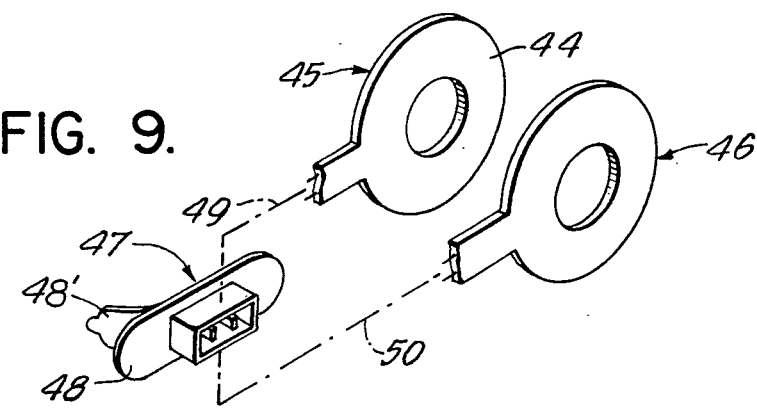
FIG. 9 is a view similar to those of FIGS. 1 and 7, to show another assembly alternative.

FIG. 9 illustrates a third embodiment which represents a unit-handling assembly of two coil units 45-46, each of which is independently mountable to the body of the patient. A plug-connection unit 47 has its own separate mounting strip 48 which extends longitudinally on both sides of ultimate electrical supply connection thereto. Unit 47 is coated with a layer of pressure-sensitive adhesive on its smooth side, the adhesive being protected by a separable cover 48' of release material, and flat flexible lead-cable connections 49-50 to the respective coil units 45-46 complete the unit-handling assembly. The ultimately facing surfaces of coil units 45-46 are provided with adhesive coatings, protected as at 44 and correctly related to the desired ultimate flux-aiding excitation of units 45-46. Orthopedic-cast application over units 45-46-47 that have been correctly oriented to the afflicted body will be understood to proceed conventionally, so that these units and their flexible interconnections become fixed and integrated in the completed cast, with external access to excitation signals, as via plug connection 13 to signal generator 15.

The described devices, configurations and techniques will be seen to achieve all stated objects. For the rigidly connected double-coil embodiment of FIG. 1, there can be no ambiguity of electrical connections to assure flux-aiding relation between the coils; therefore, the orthopedic surgeon requires no significant change in his technique of cast development, and the patient becomes no more encumbered than if he were subjected to a conventional cast. The same may be said as to the dual employment of coil units of FIGS. 2 or 3, in that known plug and receptacle components at 29-29' (and 27-27') can be pre-wired to assure ultimate flux-aiding excitation of the involved two coils, when adhered to the body. Finally, by applying the adhesive coats 43 to surfaces consistent with pre-wiring inter-coil connections, the desired flux-aiding relation is assured, and no burden of wiring ambiguity or responsibility is placed upon the surgeon.

While the invention has been described in detail for various illustrative embodiments, it will be understood that modifications may be made without departing from the scope of the invention. For example, the use of pressure-sensitive coatings and peel-off protection is preferred, but unambiguous self-adherent coil elements may also be available through use of adhesive tape, wherein say a length of such tape of substantially twice the outer diameter of a coil unit as in FIG. 8 (but without layer 43 and sheet 44) is instead applied along a diameter of the coil-unit surface that is not visible in FIG. 8, there being enough tape extending beyond both ends of the diameter, to enable wrap around onto the surface exposed in FIG. 8, so that the surgeon need only peel up the ends of the tape and apply them to the patient, in order to hold the desired temporary placement of the coil unit on the body.

It will be understood that the described parallel connections in FIGS. 5 and 6 are purely illustrative, in that series connections should be made if greater electrical resistance is desired.

What is claimed is:

1. An electromagnetic bodytreatment device for surgically non-invasive modification of the growth, repair and maintenance behavior of living tissues and cells by a specific and selective change in electrical environment, comprising, as an article of manufacture, an insert for an orthopedic cast or the like to enclose an afflicted body-member region and an adjacent unafflicted body-member region, said insert comprising a stiffly flexible elongate strip of magnetically transparent material, a single multiturn electrical coil of initially generally flat annular configuration and fixed to one side of said strip, with said strip extending in at least one generally radially outward direction from said coil and to a longitudinally offset location removed from said coil, said strip being elongate to the extent of at least the coil diameter and thus sufficiently elongate to enable a stabilizing wrapped application thereof to the unafflicted body-member region while positioning the axis of the coil for intersection with the afflicted region, said coil having leads mounted to said strip and extending to said offset location, the annular configuration of said coil establishing a circular central region within which magnetic flux may be concentrated upon application of an electrical signal via said leads, and means including an externally accessible cable connector carried by said strip at said location and connected to said leads for electrically exciting said coil with a therapeutically beneficial electrical signal, whereby in the course of conventionally applying a cast for orthopedic support of an afflicted limb or other body region, said insert may be embedded in the cast in longitudinal overlap of said coil and strip to leave externally exposed essentially only said cable connector.

2. The article of claim 1, in which said lastdefined means includes an externally exposed connector that is detachable at said offset location.

3. The article of claim 1, in which said lastdefined means includes detachable connector components, one of which components is fixed to said one side of said strip and includes a peripheral wall extending outward of said strip to at least the anticipated cast thickness.

4. The article of claim 1, in which said coil is of axial thickness substantially less than radial extent between inner and outer radial limits.

5. The article of claim 1 or claim 4, in which said coil is flexibly deformable out of its initial substantially flat shape and into local substantial conformance with the body-surface at the specifically afflicted region.

6. The article of claim 1, in which said coil is one of two like coils, there bing a stiffly flexible strip of magnetically transparent material extending from the second coil and generally parallel to the elongate strip which extends from said one coil, and a stiffly flexible strip of magnetically transparent material so connected to said firstmentioned and second-mentioned strips as to position said coils on opposite sides of the afflicted region and with the axes of said coils in substantial alignment, said last-defined strip having arched local conformance to body-surface curvature between the opposite body sides served by said coils.

7. The article of claim 6, in which leads for the second coil are carried by said strips and are interconnected for coaction in flux-aiding fashion through the specifically afflicted region.

8. The article of claim 1, in which said coil is an initially flat radially expanding spiral of conductive turns bonded to a supporting substrate of flexible material that is magnetically transparent, said substrate being connected to said strip.

9. The article of claim 8, in which said coil is a printed-circuit application on one side of said substrate.

10. The article of claim 9, in which said printedcircuit application is one of two coil components, the second of which is on the other side of said substrate, and the leads to said coil components being connected in flux-aiding relation.

11. The article of claim 9, in which said substrate and printed-circuit application comprises one of two components of said coil, said components being flexibly retained in axial registration and being lead-connected in flux-aiding relation.

12. The article of claim 9, in which said strip and substrate are one and the same, and in which said printed-circuit application includes leads for said coil.

13. The article of claim 1, in which the width of the extending part of said strip is less than the outer radius of said coil and is connected to said coil with the longitudinal centerline of said strip in radially offset relation to the axis of said coil.

14. The article of claim 1, in which the width of the extending part of said strip is less than the outer radius of said coil and is connected to said coil with the longitudinal centerline of said strip in intersecting alignment with the axis of said coil.

15. As an article of manufacture, a flexible substrate sheet of non-conductive magnetically transparent material, a first printed-circuit electrically conductive coil element on one of the surfaces of said sheet, a second printed-circuit electrically conductive coil element on the other surface of said sheet and in substantial axial register with said first coil element, each said coil element comprising multiple turns of spirally expanding radius, there being two lead-connection ends of each coil element, and lead means connecting the lead-connection ends of said coil elements for concurrent coil excitation in flux-aiding relation.

16. As an article of manufacture, a first flexible substrate sheet of non-conductive magnetically transparent material, and a printed-circuit electrically conductive coil element on one of the surfaces of said sheet, said coil element comprising multiple turns of spirally expanding radius, a second flexible substrate sheet of non-conductive magnetically transparent material with a printed-circuit electrically conductive coil element on one of the surfaces of the second sheet, said sheets being flexibly laminated to each other with their coil elements in substantial axial register, and lead means connecting said coil elements for concurrent excitation in flux-aiding relation.

17. The article of claim 15 or claim 16, in which a pressure-sensitive adhesive layer coats one otherwise exposed surface of the article, and a protective sheet of release material removably adhered to said adhesive layer.

18. An electromagnetic bodytreatment device for surgically non-invasive modification of the growth, repair and maintenance behavior of living tissues and cells by a specific and selective change in electrical environment, comprising, as an article of manufacture, plural electrical components with flexible electrical connection therebetween; one of said components comprising a flexible substrate sheet of non-conductive magnetically transparent material, and a printed-circuit electrically conductive coil element on one of the surfaces of said sheet, said coil element comprising multiple turns of spirally expanding radius, a coat of pressure-sensitive adhesive on one of the surfaces of said circuit-printed sheet, and a protective sheet of release material removably adhered to said adhesive coat; the other of said components comprising a stiffly flexible strip of magnetically transparent material having a coat of pressuresensitive adhesive material on one surface thereof, a protective sheet of release material removably adhered to said adhesive coat, and an externally accessible electrical connector carried by said strip and projecting outward from the other surface thereof, said connector being electrically connected to said coil element via the flexible electrical connection between said components and adapted for exciting said coil element with a therapeutically beneficial electrical signal.

19. An electromagnetic bodytreatment device for surgically non-invasive modification of the growth, repair and maintenance behavior of living tissues and cells by a specific and selective change in electrical environment, comprising, as an article of manufacture, plural electrical components with flexible electrical-connection means therebetween; each of two of said components comprising a flexible substrate sheet of non-conductive magnetically transparent material, and a printed-circuit electrically conductive coil element on one of the surfaces of said sheet, said coil element comprising multiple turns of spirally expanding radius, a coat of pressure-sensitive adhesive on one of the surfaces of said circuit-printed sheet, and a protective sheet of release material removably adhered to said adhesive coat; and a third of said components comprising a stiffly flexible strip of magnetically transparent material having a coat of pressure-sensitive adhesive material on one surface thereof, a protective sheet of release material removably adhered to said adhesive coat, and an externally accessible electrical connector carried by said strip and projecting outward from the other surface thereof, said connector being electrically connected to said coil elements via said flexible electrical-connection means and adapted for exciting said coil elements with a therapeutically beneficial electrical signal, and said coil elements being connected in fluxaiding relation when the adhesively coated surfaces of said substrate sheets are in mutually facing opposition.

* * * * *